US00PP36077P2

(12) United States Plant Patent
Ichiba

(10) Patent No.: US PP36,077 P2
(45) Date of Patent: Aug. 20, 2024

(54) ***SCABIOSA* PLANT NAMED 'Ichbu2005'**

(50) Latin Name: ***Scabiosa* hybrid**
Varietal Denomination: Ichbu2005

(71) Applicant: Kaori Ichiba, Tokyo (JP)

(72) Inventor: Kaori Ichiba, Tokyo (JP)

( * ) Notice: Subject to any disclaimer, the term of this patent is extended or adjusted under 35 U.S.C. 154(b) by 0 days.

(21) Appl. No.: 18/517,441

(22) Filed: Nov. 22, 2023

(30) Foreign Application Priority Data

Jul. 17, 2023 (QZ) ..... PBR 2023/1514

(51) Int. Cl.
*A01H 5/02* (2018.01)
*A01H 6/00* (2018.01)

(52) U.S. Cl.
USPC ..... Plt./478

(58) Field of Classification Search
USPC ..... Plt./478
See application file for complete search history.

*Primary Examiner* — Susan McCormick Ewoldt
(74) *Attorney, Agent, or Firm* — Penny J. Aguirre

(57) ABSTRACT

A new cultivar of *Scabiosa* plant named 'Ichbu2005' that is characterized by its inflorescences that are an intense and deep purple-blue color and its good tolerance to cold and heat.

3 Drawing Sheets

Botanical classification:
*Scabiosa* hybrid.
Variety denomination: 'Ichbu2005'.

CROSS-REFERENCE TO A RELATED APPLICATION

This application claims priority to European Community Plant Variety Office (CPVO) Plant Breeder's Rights Application No. 2023/1514 filed on Jul. 17, 2023, under 35 U.S.C. 119(f), the entire contents of which is incorporated by reference herein.

BACKGROUND OF THE INVENTION

The present invention relates to a new and distinct cultivar of *Scabiosa* of hybrid origin, botanically known as *Scabiosa* 'Ichbu2005' and will be referred to hereinafter by its cultivar name, 'Ichbu2005'.

The new cultivar was derived from a controlled breeding program by the Inventor in Hachioji-shi, Tokyo, Japan. The Inventor made a cross in July of 2019 between an unnamed and unpatented proprietary plant in the Inventor's breeding program, reference name "Non-name-my Blue", as the female parent that was pollinated with a mixture of pollen from the Inventor's breeding program. The male parent is therefore unknown. The Inventor selected 'Ichbu2005' as a single unique plant in May of 2020 from amongst the seedlings that resulted from the above cross.

Asexual propagation of the new cultivar was first accomplished by the Inventor by stem cuttings in October of 2019 in Tokyo, Japan. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of 'Ichbu2005'.

These characteristics in combination distinguish 'Ichbu2005' as a new and distinct cultivar of *Scabiosa*.

1. 'Ichbu2005' exhibits inflorescences that are an intense and deep purple-blue color.
2. 'Ichbu2005' exhibits good tolerance to cold and heat.

The female parent of 'Ichbu2005' differs from 'Ichbu2005' in having a taller plant height, longer stems, and inflorescences that are lighter in color. 'Ichbu2005' can be most closely compared to the *Scabiosa* cultivars 'Butterfly Blue' (not patented) and 'ICHPIN' (U.S. Plant Pat. No. 28,303). 'Butterfly Blue' is similar to 'Ichbu2005' in having inflorescences that are purple-blue in color. 'Butterfly Blue' differs from 'Ichbu2005' in having a less neat and less tidy plant habit, inflorescences that are paler and less intense purple-blue in color, and a less tolerance to cold and heat. 'ICHPIN' differs from 'Ichbu2005' in having inflorescences that are bright pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Walter Blom Plants, Perfect Plants (ebay), and Hishtill (linkedin).

BRIEF DESCRIPTION OF THE DRAWINGS

The accompanying color photographs illustrate the overall appearance and distinct characteristics of a two-year-old plant of the new *Scabiosa* as grown outdoors in a 17-cm container in Hillegom, The Netherlands. The photograph in FIG. 1 provides a side view of 'Ichbu2005' in bloom. The photograph in FIG. 2 provides a close-up view of an inflorescence of 'Ichbu2005'. The photograph in FIG. 3 provides a close-up view of the foliage of 'Ichbu2005'. The colors in the photographs may differ slightly from the color values cited in the detailed botanical description, which accurately describes the colors of the new *Scabiosa*.

DETAILED BOTANICAL DESCRIPTION

Figure 1:
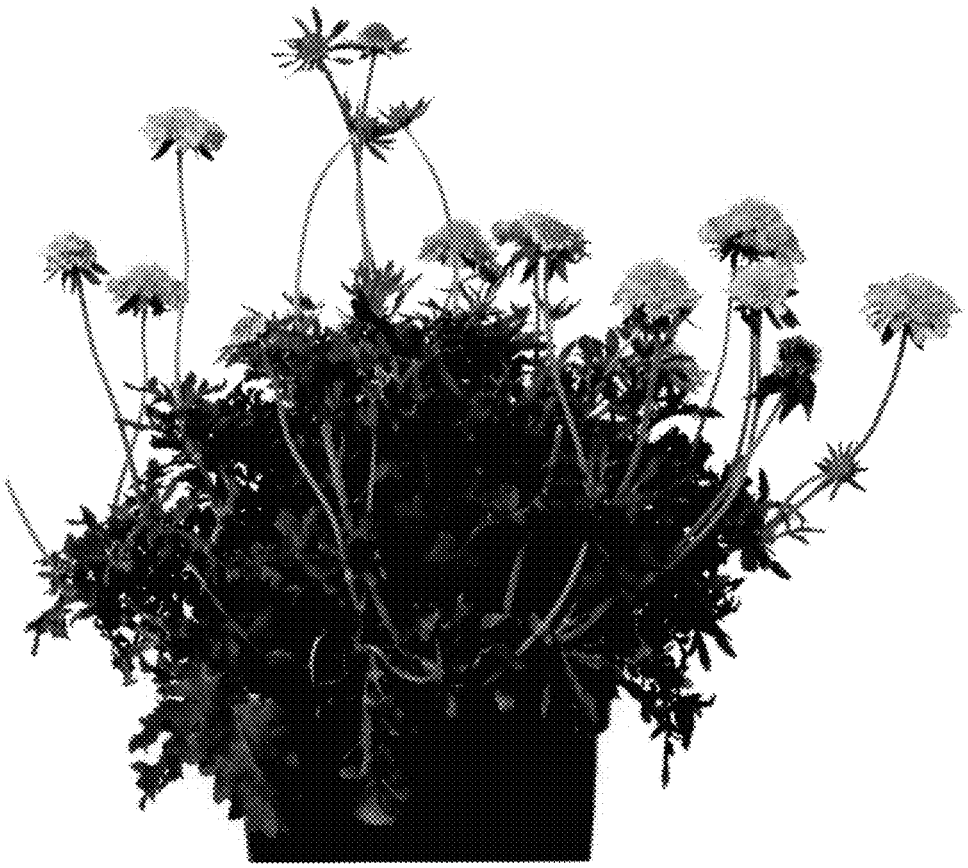
Figure 2:
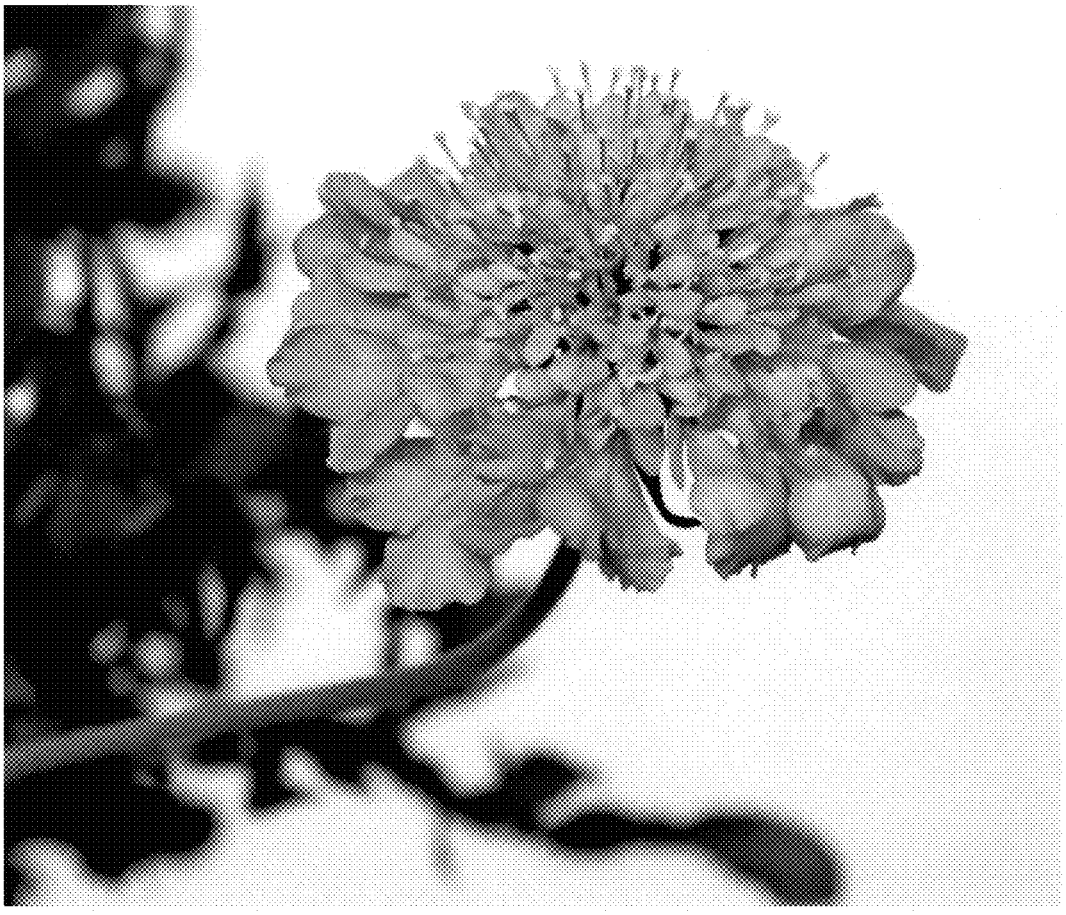
Figure 3:
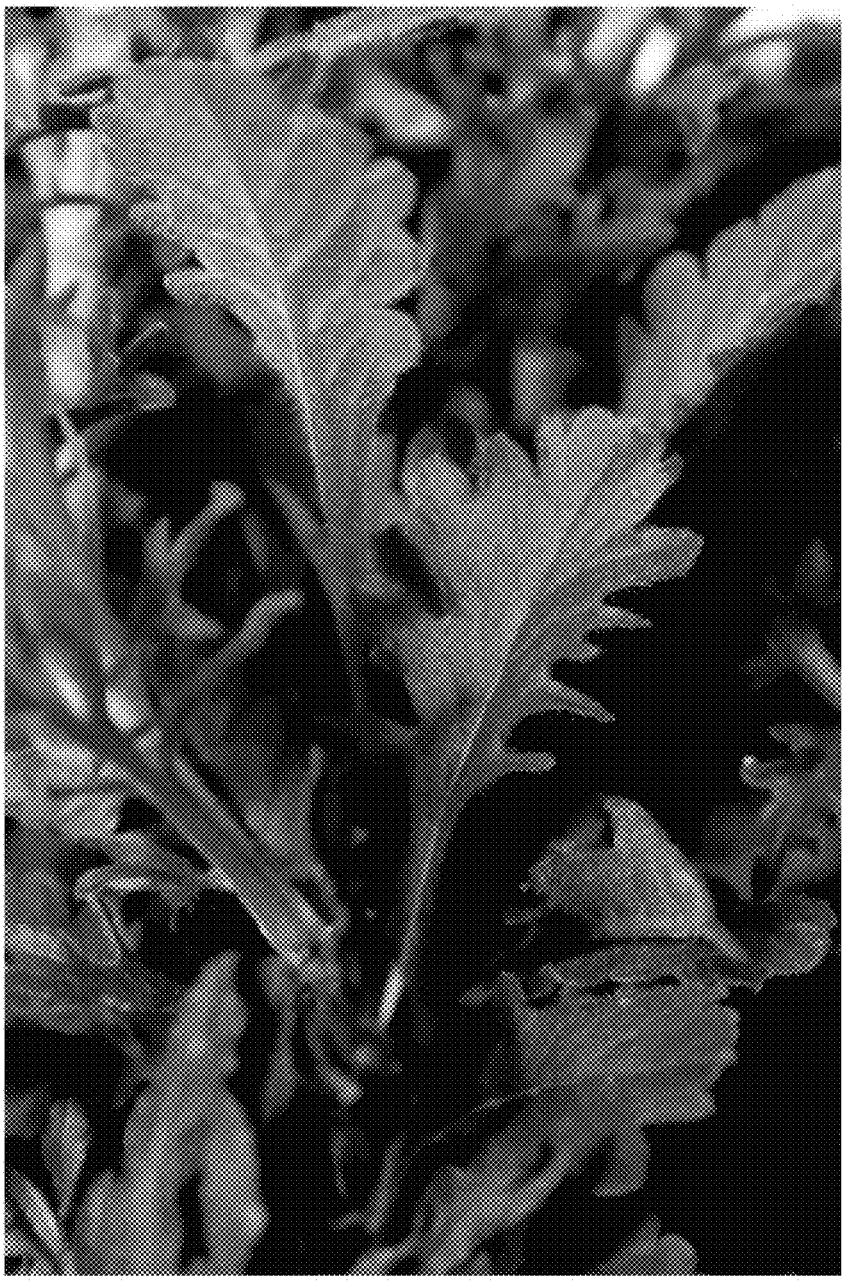

The following is a detailed description of 2-year-old plants of the new cultivar as grown outdoors in 17-cm containers in Hillegom, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General Description:

*Blooming period*.—Late spring into summer in The Netherlands.

*Plant habit*.—Herbaceous perennial, upright with extended flowering stems.

*Height and spread*.—Average of 18.3 cm in height (top of foliar plane), 40.8 cm in height (top of floral plane), 41.8 cm in diameter as a 2-year-old plant grown in a container.

*Cold Hardiness*.—Cold hardy at least to U.S.D.A Zone 6.

*Disease and pest resistance*.—No susceptibility or resistance to diseases or pests has been observed.

*Root description*.—Fine and fibrous.

*Propagation*.—Stem cuttings.

*Root development*.—Roots initiate in 14 to 20 days under greenhouse conditions and rooting cutting plugs will develop to a flowering plant in 15 weeks.

*Growth rate*.—Moderate.

Stem Description:

*Stem shape*.—Rounded.

*Stem color*.—Developing; 144A, mature; 144A, base 145A, old stems and bark; 143B, upper surface tinged 147A.

*Stem size*.—12.7 cm in length, 4 mm in diameter.

*Internodes*.—3.1 cm in length, 144A, tinged 177D.

*Stem surface*.—Slightly glossy, densely covered with short soft hairs that are 0.5 mm in length, N155A in color.

*Stem strength*.—Strong.

*Branching habit*.—Main stems grow from the base with lateral stems, main branches; 17, lateral branches; 2 per main branch.

Foliage Description:

*Leaf division*.—Single.

*Leaf shape*.—Basal and lower; runcinate, upper; broadly ovate to broadly obovate.

*Leaf base*.—Basal and lower; runcinate, upper; broadly ovate to broadly obovate.

*Leaf apex*.—All leaves attenuate.

*Leaf margin*.—Basal and lower; pinnatifid to pinnatisect, moderately undulate, lobes divergent, obtuse tips, upper; laciniate, lobes divergent, acute tips.

*Leaf venation*.—Pinnate, color on upper surface 151C, lower surface 146B and 146C.

*Leaf attachment*.—Petiolate.

*Leaf arrangement*.—Opposite.

*Leaf surface*.—All leaves; both surfaces slightly glossy, soft to the touch, margins densely covered with short soft hairs, 0.5 mm to 1 mm in length, 156D in color.

*Leaf color*.—All leaves; young upper surface 137C, young lower surface 143C, mature upper surface NN137A, mature lower surface 147B.

*Leaf size*.—Basal and lower; 6.5 cm in length, 4.2 cm in width, upper; 5.2 cm in length, 5 cm in width.

*Leaf mumber*.—Average of 10 per main branched stem.

*Leaf fragrance*.—None.

*Internode length*.—3.1 cm.

*Petiole*.—Flattened, basal and lower; 3.6 cm in length, 3.5 mm in diameter, upper; 5 mm in length, 2.5 mm in diameter.

Flower Description:

*Inflorescence type*.—Terminal capitulum.

*Lastingness of inflorescence*.—Average of one week, self-cleaning.

*Inflorescence size*.—Average of 3 cm in height, 5.2 cm in width.

*Inflorescence fragrance*.—None.

*Inflorescence number*.—An average of 1 per stem.

*Flower quantity*.—An average of 750 per plant.

*Flower aspect*.—Outward to upright.

*Flower buds*.—Average of 6 mm in length, 3 mm in diameter, 145B in color, obovate in shape.

*Corolla*.—Funnelform, marginal flowers; lower 25% fused into tube, 1.6 cm in height, 1.8 cm in diameter, 2.1 cm in depth, petals; 5, rotate, 1 whorl, 2 identical upper petals, 2 identical lateral petals, 1 lower petal, matte surface, smooth and glabrous, base is densely covered with very short pubescent hairs 0.3 mm in length, 155C in color, upper and lateral petals obovate in shape, lower petal spathulate, 3-lobed, obtuse tips, base fused, entire margins, low to medium undulate, both surfaces smooth and glabrous, non-rugose, matte, lower surface moderately covered with very short pubescence, 0.2 mm in length, too small to measure color, size; upper 2 petals average of 5 mm in length, 6 mm in width, lateral petals 1 cm in length, 9 mm in width, lower petals 1.2 cm in length, 1.1 cm in width, color; when opening and fully open upper surface 90C and 90D, when opening and fully open lower surface N88D, changing towards the tube to 91B, throat color 85D, tube; both surfaces 155C in color, 5 mm in length, 1.5 mm in diameter, densely covered in short pubescent hairs; 0.3 mm in length, 155C in color, central flowers; lower 60% fused into the tube, 7 mm in height, 6 mm in diameter, 1.2 cm in depth, petals; 5, rotate, 1 whorl, 2 identical upper petals, 2 identical lateral petals, 1 lower petal, matte surface, smooth and glabrous, base is densely covered with very short pubescent hairs 0.3 mm in length, 155C in color, upper and lateral petals ovate, lower petals obovate, obtuse tips, base fused, entire margins, low to medium undulate, both surfaces smooth and glabrous, non-rugose, matte, lower surface moderately covered with very short pubescence, 0.2 mm in length, too small to measure color, size; upper 2 petals average of 3 mm in length, 2 mm in width, lateral petals 3.5 mm in length, 2 mm in width, lower petals 5 mm in length, 2 mm in width, color; when opening upper and lower surface N88C, when fully open upper surface N88C, lateral and upper petals 91C, when fully open lower surface 85B, lateral and upper petals 85D, throat color 85D, tube; both surfaces 155C in color, 4 mm in length, 1.5 mm in diameter, densely covered in short pubescent hairs; 0.3 mm in length, 155C in color.

*Calyx*.—Rotate, 6 mm in length, 9 mm in diameter.

*Sepals*.—Varying between 4 and 6, average of 5, upper surface smooth and glabrous, lower surface moderately covered with very short glandular hairs, average of 0.2 mm in length, NN155D in color, linear in shape, entire margins, narrow acuminate apex, broadly cuneate base, 6 mm in length, 0.5 mm in width, color; young and mature upper and lower surfaces N186A, base 187C.

*Peduncles*.—17.7 cm in length and 3 mm in diameter, held in a vertical angle, strong, matte surface, 143B in color, densely covered with short soft hairs, an average of 0.5 mm in length, 157D in color.

*Pedicels*.—none, individual flowers sessile.

*Involucral bracts*.—10, arrangement is whorl around flower head, narrow oblong in shape, acute apex, broadly cuneate base, 6 mm in length, 3 mm in width, surfaces are moderately pubescent with thin hairs that are an average of 0.5 mm in length and NN155D in color.

Reproductive Organs:

*Gynoecium*.—Pistil; 1.5 cm in length, stigma; 0.8 mm in diameter, cleft in shape, 76D in color, style; 1.4 cm in length, color 76A, N155A base, ovary; 144B in color.

*Androecium*.—Stamens; 3, filaments; 1 mm in length, NN155D in color, anthers; elliptic, 1.5 mm in length, 0.7 mm in width, 75C in color, pollen; low in quantity, 163C in color.

*Fruit seeds*.—None observed to date.

It is claimed:

1. A new and distinct cultivar of *Scabiosa* plant named 'Ichbu2005' as herein illustrated and described.

* * * * *